US009597367B2

(12) United States Patent
Wolfe et al.

(10) Patent No.: US 9,597,367 B2
(45) Date of Patent: Mar. 21, 2017

(54) METHODS FOR IMPROVING MUSCLE AND HEART FUNCTION

(71) Applicant: Board of Trustees of the University of Arkansas, Little Rock, AR (US)

(72) Inventors: Robert R. Wolfe, Little Rock, AR (US); Jeanne Wei, Little Rock, AR (US)

(73) Assignee: BIOVENTURES, LLC, Little Rock, AR (US)

( * ) Notice: Subject to any disclaimer, the term of this patent is extended or adjusted under 35 U.S.C. 154(b) by 339 days.

(21) Appl. No.: 14/256,323

(22) Filed: Apr. 18, 2014

(65) Prior Publication Data

US 2014/0315788 A1 Oct. 23, 2014

Related U.S. Application Data

(60) Provisional application No. 61/814,034, filed on Apr. 19, 2013.

(51) Int. Cl.
| | | |
|---|---|---|
| A61K 31/197 | (2006.01) | |
| A61K 31/198 | (2006.01) | |
| A61K 38/10 | (2006.01) | |
| A61K 38/16 | (2006.01) | |

(52) U.S. Cl.
CPC ............ *A61K 38/10* (2013.01); *A23L 33/175* (2016.08); *A61K 31/197* (2013.01); *A61K 31/198* (2013.01); *A61K 38/164* (2013.01)

(58) Field of Classification Search
CPC .......... A23L 1/48; A23L 1/293; A23L 33/175; A61K 31/197; A61K 31/198
See application file for complete search history.

(56) References Cited

U.S. PATENT DOCUMENTS

| | | | | | |
|---|---|---|---|---|---|
| 5,817,329 | A * | 10/1998 | Gardiner | ................ | A23L 1/3051 424/439 |
| 7,288,570 | B2 * | 10/2007 | Verlaan | .................. | A23L 1/3051 514/561 |
| 7,790,688 | B2 * | 9/2010 | Wolfe | ................... | A61K 31/198 426/656 |
| 8,846,759 | B2 * | 9/2014 | Luiking | ................... | A23L 1/296 514/561 |
| 2003/0162241 | A1 * | 8/2003 | Pittner | ...................... | C12Q 1/32 435/25 |
| 2008/0268038 | A1 * | 10/2008 | Wolfe | ................... | A23L 1/3051 424/452 |
| 2009/0297689 | A1 * | 12/2009 | Edens | ........................ | A23L 1/29 426/656 |
| 2010/0267831 | A1 * | 10/2010 | Kobayashi | ............ | A23L 1/3051 514/561 |
| 2012/0245331 | A1 * | 9/2012 | Takakura | .............. | C07K 14/375 530/402 |
| 2013/0203701 | A1 * | 8/2013 | Leighton | ................ | A61K 31/20 514/62 |
| 2013/0210780 | A1 * | 8/2013 | Jourdan | .................. | A23L 1/296 514/167 |
| 2014/0343112 | A1 | 11/2014 | Ferrando et al. | | |

FOREIGN PATENT DOCUMENTS

WO 2013/075095 A1 5/2013

OTHER PUBLICATIONS

Katsanos et al. A high proportion of leucine is required for optimal stimulation of the rate of muscle protein synthesis . . . American Journal of Physiology. Endocrinology and Metabolism. 2006. vol. 291, pp. E381-E387.*
Office Action from related U.S. Appl. No. 14/359,213, dated Oct. 29, 2015; 15 pgs.
Notice of Allowance from related U.S. Appl. No. 14/359,213, dated Mar. 16, 2016; 8 pgs.
Bohe et al., "Human muscle protein synthesis is modulated by extracellular, not intramuscular amino acid availability: a dose-response study", J Physiol, 2003, pp. 315-324, vol. 552.1.
Ferrando et al., "EAA supplementation to increase nitrogen intake improves muscle function during bed rest in the elderly", Clinical Nutrition, 2010, pp. 18-23, vol. 29, No. 1.
Fiatarone et al., "Exercise Training and Nutritional Supplementation for Physical Frailty in Very Elderly People", The New England Journal of Medicine, 1994, pp. 1769-1775, vol. 330, No. 25.
Gapeyeva et al., "Quadriceps femoris muscle voluntary isometric force production and relaxation characteristics before and 6 months after unilateral total knee arthroplasty in women", Knee Surg Sports Traumatol Arthrose, 2007, pp. 202-211, vol. 15, No. 2.
International Search Report and Written Opinion from related International Application No. PCT/US2012/065842, dated Feb. 7, 2013; 11 pgs.
University of Arkansas for Medical Sciences, "Essential Amino Acid Supplementation for Recovery from Hip Surgery: Supporting clinical data", [online] Jul. 20, 2010 (retrieved Jan. 2, 2013]. Available on the internet: <URL: http://www.ibridgenetwork.org/uams/essential-amino-acid-supplementation-for-recovery-from-hip-su>.
Unver et al., "Ability to Rise Independently from a Chair During 6-month Follow-Up After Unilateral and Bilateral Total Knee Replacement", J. Rehabil Med, 2005, pp. 385-387, vol. 37, No. 6.

\* cited by examiner

*Primary Examiner* — Jeffrey E Russel
(74) *Attorney, Agent, or Firm* — Polsinelli PC

(57) ABSTRACT

The present invention encompasses combinations comprising a plurality of amino acids, formulations thereof for use in humans and animals, as well as methods for increasing muscle protein synthesis, muscle strength, and/or muscle function in a subject with chronic heart failure, cardiac cachexia or a combination thereof.

5 Claims, 6 Drawing Sheets

US 9,597,367 B2

METHODS FOR IMPROVING MUSCLE AND HEART FUNCTION

CROSS REFERENCE TO RELATED APPLICATIONS

The present non-provisional utility application claims priority to U.S. Provisional Patent Application No. 61/814,034, entitled "Methods For Improving Heart Function, filed on filed Apr. 19, 2013, and which is hereby incorporated by reference in its entirety.

FIELD OF THE INVENTION

The present invention encompasses a combination comprising a plurality of amino acids, formulations thereof for use in humans and animals, as well as methods for increasing muscle protein synthesis, muscle strength, and/or muscle function.

BACKGROUND OF THE INVENTION

The decline in muscle mass, strength and function that occurs with aging, especially in older persons with chronic heart failure, as well as the impact of those changes on health and quality of life, is well documented. Whereas the effectiveness of resistance exercise training in improving strength, is also clear, <30% of all adult North Americans exercise regularly, and 50% of those who start an exercise program drop out within the first six months. Additional approaches are necessary to effectively ameliorate the loss of muscle mass and strength that occurs with aging.

Amino acids are potent stimulators of muscle protein synthesis in both the young and elderly. However, the anabolic response to a mixed meal containing both amino acids and carbohydrates is diminished in elderly individuals. It is therefore possible that the loss of muscle mass and strength that occurs with aging may be due, in part, to an intake of protein that is less than optimal. If this is the case, ingestion of a nutritional supplement containing amino acids may be a practical approach to improving muscle mass and strength in the elderly.

SUMMARY OF THE INVENTION

One aspect of the invention encompasses a combination comprising phenylalanine, valine, threonine, tryptophan, methionine, leucine, isoleucine, lysine, histidine, citrulline and L-carnitine in a w/w ratio of about 4:about 6:about 5:about 2:about 2:about 25:about 7:about 10:about 1:about 8:about 3, respectively.

Another aspect of the invention comprises a combination listed in Table A, Table B, or Table C.

Another aspect of the invention comprises a method for increasing muscle protein synthesis, increasing muscle strength, increasing muscle function, or a combination thereof, the method comprising administering to a subject a combination comprising phenylalanine, valine, threonine, tryptophan, methionine, leucine, isoleucine, lysine, histidine, citrulline and L-carnitine in a w/w ratio of about 4:about 6:about 5:about 2:about 2:about 25:about 7:about 10:about 1:about 8:about 3, respectively. A subject may have chronic heart failure, cardiac cachexia or a combination thereof. Alternatively a subject may be at risk for muscle atrophy.

Another aspect of the invention comprises a method for increasing muscle protein synthesis, increasing muscle strength, increasing muscle function, or a combination thereof, the method comprising administering to a subject a combination listed in Table A, Table B or Table C. A subject may have chronic heart failure, cardiac cachexia or a combination thereof. Alternatively a subject may be at risk for muscle atrophy.

Other aspects and iterations of the invention are described more thoroughly below.

DETAILED DESCRIPTION OF THE INVENTION

Figure 1:
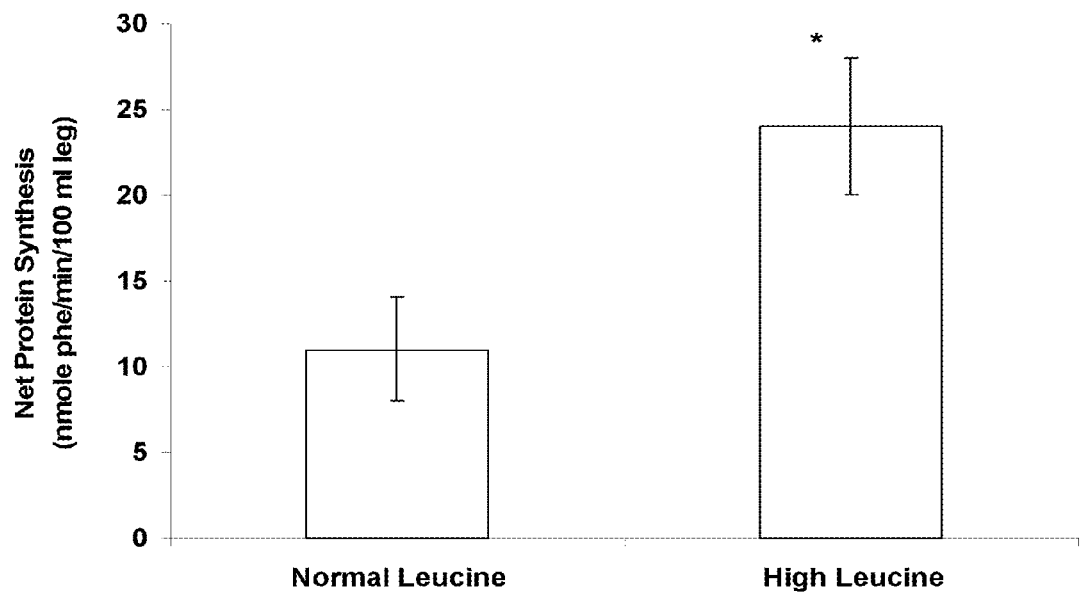
FIG. 1 depicts graphs showing a combination of essential amino acids increases net protein synthesis in the leg muscle of healthy human volunteers over the age of 65 years. The y-axis depicts the increase above basal in the balance between protein synthesis and breakdown (net protein synthesis). Volunteers ingested 6.7 grams of a mixture of EAAs in the profile of whey protein (Normal Leucine) or a mixture of the same amount of EAAs with 40% leucine (High Leucine), with the proportionate contribution of the other EAAs decreased. Muscle protein synthesis was measured using a stable isotope tracer technique that was based on blood sampling from indwelling catheters in the femoral artery and vein and muscle tissue sampling by needle biopsy.

The present invention provides a combination comprising a plurality of amino acids. When administered to a subject, a combination of the invention produces an effective response in the subject. An effective response can be an increase in muscle protein synthesis, an increase in muscle strength, an increase in muscle function, or a combination thereof. Also contemplated are compositions comprising a combination of the invention formulated for use in humans and animals. Advantageously, a combination of the invention produces an effective response when administered to a subject, even in the absence of an exercise program. Additional aspects to the invention are described in further detail below.

I. Combination Comprising a Plurality Amino Acids

The present invention provides a combination comprising a plurality of amino acids. An amino acid can be a proteinogenic amino acid or a non-proteinogenic amino acid. In an aspect, a plurality of amino acids comprises two or more proteinogenic amino acids and, optionally, one or more non-proteinogenic amino acids. The proteinogenic amino acids are phenylalanine, valine, threonine, tryptophan, methionine, leucine, isoleucine, lysine, histidine, alanine, arginine, asparagine, aspartic acid, cysteine, glutamic acid, glutamine, glycine, ornithine, proline, selenocysteine, serine and tyrosine. A combination of the invention may comprise any combination of 2, 3, 4, 5, 6, 7, 8, 9, 10, 11, 12, 13, 14, 15, 16, 17, 18, 19, 20, 21, or 22 proteinogenic amino acids. A non-proteinogenic amino acid does not participate in peptide synthesis, and may or may not be naturally occurring. The non-proteinogenic amino acids far outnumber the proteinogenic amino acids, approaching at least 300. See, for example, Peptides from A to Z: A Concise Encyclopedia, 2008, Wiley-VCH Verlag GmbH & Co. Combinations comprising a non-proteinogenic amino acid may comprise at least 1, at least 2, at least 3, at least 4, at least 5, at least 6, at least 7, at least 8, at least 9, or at least 10 or more non-proteinogenic amino acids.

In another aspect, a plurality of amino acids comprises one or more essential amino acids. Applicants have found the preferential use of essential amino acids compared to non-essential amino acids in a combination of the invention reduces the amount of amino acids that must be given to elicit an effective response. An essential amino acid (EAA) is an amino acid that cannot be synthesized de novo by a subject, and therefore must be supplied in its diet. The amino acids regarded as essential for humans are phenylalanine, valine, threonine, tryptophan, methionine, leucine, isoleucine, lysine, and histidine. In some embodiments, a combination of the invention comprises phenylalanine, valine, threonine, tryptophan, methionine, leucine, isoleucine, lysine, and histidine.

When a combination of the invention comprises all nine essential amino acids, the nine essential amino acids are at least about 80% of the total weight of the combination. For example, the nine essential amino acids can be at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94, at least about 95, at least about 96%, at least about 97%, at least about 98%, at least about 99% of the total weight of the combination. Alternatively, the nine essential amino acids can be about 80%, about 81%, about 82%, about 83%, about 84%, about 85%, about 86%, about 87%, about 88%, about 89%, about 90%, about 91%, about 92%, about 93%, about 94, about 95, about 96%, about 97%, about 98%, about 99%, or about 100% of the total weight of the combination. In another alternative, the nine essential amino acids can be about 80% to about 90%, or about 90% to about 100% of the total weight of the combination. In still another alternative, the nine essential amino acids can be about 80% to about 95%, or about 85% to about 100% of the total weight of the combination. In a different alternative, the nine essential amino acids can be about 85% to about 95% of the total weight of the combination. In a still different alternative, the nine essential amino acids can be about 80% to about 85%, about 85% to about 90%, about 90% to about 95%, or about 95% to about 100% of the total weight of the combination. In yet another alternative, the nine essential amino acids can be about 80% to about 100% of the total weight of the combination.

In another aspect, a combination of the invention has a high proportion of leucine compared to the total amount of all the EAAs in the combination. In some embodiments, the percentage of leucine is about 30% to about 40% by weight of all the EAAs. In a preferred embodiment, the percentage of the total EAAs that is leucine is about 35%, about 36%, about 37%, about 38%, about 39% or about 40% by weight of all the EAAs. In another preferred embodiment, the percentage of the total EAAs that is leucine is about 35% to about 40% by weight of all the EAAs.

In another aspect, a plurality of amino acids comprises one or more essential amino acids, and one or more conditionally essential amino acids and/or one or more conditionally essential amino acid precursors. The amino acids arginine, cysteine, glycine, glutamine, proline, serine and tyrosine are considered conditionally essential, meaning they are not normally required in the diet, but must be supplied exogenously to specific populations that do not synthesize them in adequate amounts. For example, the body produces sufficient arginine to satisfy metabolic requirements under normal conditions. Therefore, arginine supplementation is not necessary to stimulate muscle protein synthesis for many subjects. However, in certain clinical circumstances, including in elderly with heart failure, endogenous arginine production is inadequate to meet all demands. For such a population, it is advantageous for combinations of the invention to comprise arginine, or a precursor of the amino acid arginine. The term "amino acid precursor" refers to a metabolic precursor of an amino acid. For example, serine is a metabolic precursor of cysteine and glycine; and 3-phosphoglycerate is a metabolic precursor of serine and, therefore, of cysteine and glycine too. As a second example, citrulline is a metabolic precursor of arginine. The metabolic pathways that synthesize amino acids are well known in the art, and a skilled artisan may refer to these to identify metabolic precursors of other amino acids. In some embodiments, a combination of the invention comprises phenylalanine, valine, threonine, tryptophan, methionine, leucine, isoleucine, lysine, histidine, and at least one conditionally essential amino acid. For example, the combination may comprise 1, 2, 3, 4, 5, 6, 7, 8, 9, or 10 conditionally essential amino acids. In other embodiments, a combination of the invention comprises phenylalanine, valine, threonine, tryptophan, methionine, leucine, isoleucine, lysine, histidine, and at least one conditionally essential amino acid precursor. For example, the combination may comprise 1, 2, 3, 4, 5, 6, 7, 8, 9, or 10 conditionally essential amino acid precursors. In still other embodiments, a combination of the invention comprises phenylalanine, valine, threonine, tryptophan, methionine, leucine, isoleucine, lysine, histidine, at least one non-essential amino acid and at least one conditionally essential amino acid precursor. In a preferred embodiment, a combination of the invention comprises citrulline.

When a combination of the invention comprises one or more conditionally essential amino acid and/or conditionally essential amino acid precursor, the one or more amino acid and/or amino acid precursor is no more than about 20% by weight of the combination. For example, a combination may comprise one or more conditionally essential amino acids and/or amino acid precursors in an amount that is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight of the combination. In another alternative, the one or more conditionally essential amino acids and/or conditionally essential amino acid precursors can be about 1% to about 10%, or about 10% to about 20% of the total weight of the combination. In still another alternative, the one or more conditionally essential amino acids and/or conditionally essential amino acid precursors can be about 1% to about 15%, or about 5% to about 20% of the total weight of the combination. In a different alternative, the one or more conditionally essential amino acids and/or conditionally essential amino acid precursors can be about 5% to about 15% of the total weight of the combination. In a still different alternative, the one or more conditionally essential amino acids and/or conditionally essential amino acid precursors can be about 1% to about 5%, about 5% to about 10%, about 10% to about 15%, or about 15% to about 20% of the total weight of the combination.

In another aspect, a plurality of amino acids comprises one or more non-standard amino acid. As used herein, the term "non-standard amino acid" refers to a non-proteinogenic amino acid that occurs naturally in a cell. In a cell, a non-standard amino acid is generated by modification of a proteinogenic amino acid. Non-limiting examples of non-standard amino acids include L-carnitine, GABA, hydroxyproline, hydroxylysine, pyrrolysine, selenomethionine, hypusine, L-DOPA, 2-aminobutyric acid, dehydralanine, gamma-carboxyglutamic acid. In some embodiments, a combination of the invention comprises phenylalanine, valine, threonine, tryptophan, methionine, leucine, isoleucine, lysine, histidine, and at least non-standard amino acid. For example, the combination may comprise 1, 2, 3, 4, 5, 6, 7, 8, 9, or 10 non-standard amino acids. In other embodiments, a combination of the invention comprises (i) phenylalanine, valine, threonine, tryptophan, methionine, leucine, isoleucine, lysine, and histidine; (ii) at least one conditionally essential amino acid; and (iii) at least one non-standard amino acid. In still other embodiments, a combination of the invention comprises (i) phenylalanine, valine, threonine, tryptophan, methionine, leucine, isoleucine, lysine, and histidine; (ii) at least one conditionally essential amino acid precursor; and (iii) at least one non-standard amino acid. In yet other embodiments, a combination of the invention comprises (i) phenylalanine, valine, threonine, tryptophan, methionine, leucine, isoleucine, lysine, and histidine; (ii) at least one conditionally essential amino acid; (iii) at least one conditionally essential amino acid precursor; and (iv) at least one non-standard amino acid. In preferred embodiments, the conditionally essential amino acid is citrulline and the non-standard amino acid is L-carnitine.

When a combination of the invention comprises one or more non-standard amino acid, the one or more non-standard amino acid is no more than about 20% by weight of the combination. For example, a combination may comprise one or more non-standard amino acid in an amount that is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight of the combination. In another alternative, the one or more non-standard amino acid can be about 1% to about 10%, or about 10% to about 20% of the total weight of the combination. In still another alternative, the one or more non-standard amino acid can be about 1% to about 15%, or about 5% to about 20% of the total weight of the combination. In a different alternative, the one or more non-standard amino acid can be about 5% to about 15% of the total weight of the combination. In a still different alternative, the one or more non-standard amino acid can be about 1% to about 5%, about 5% to about 10%, about 10% to about 15%, or about 15% to about 20% of the total weight of the combination.

In a preferred embodiment, a combination of the invention comprises phenylalanine, valine, threonine, tryptophan, methionine, leucine, isoleucine, lysine, and histidine in a w/w ratio of about 4:about 6:about 5:about 2:about 2:about 25:about 7:about 10:about 1, respectively. In another preferred embodiment, a combination of the invention comprises phenylalanine, valine, threonine, tryptophan, methionine, leucine, isoleucine, lysine, and histidine in a w/w ratio of about 4:about 6:about 5:about 2:about 2:about 25:about 7:about 10:about 1, respectively, wherein the nine essential amino acids are at least about 80% of the total weight of the combination. In another preferred embodiment, a combination of the invention comprises phenylalanine, valine, threonine, tryptophan, methionine, leucine, isoleucine, lysine, histidine and citrulline in a w/w ratio of about 4:about 6:about 5:about 2:about 2:about 25:about 7:about 10:about 1:about 8, respectively. In yet another preferred embodiment, a combination of the invention comprises phenylalanine, valine, threonine, tryptophan, methionine, leucine, isoleucine, lysine, histidine and citrulline in a w/w ratio of about 4:about 6:about 5:about 2:about 2:about 25:about 7:about 10:about 1:about 8, respectively, wherein the ten amino acids are at least about 95% of the total weight of the combination. In still another preferred embodiment, a combination of the invention comprises phenylalanine, valine, threonine, tryptophan, methionine, leucine, isoleucine, lysine, histidine, citrulline and L-carnitine in a w/w ratio of about 4:about 6:about 5:about 2:about 2:about 25:about 7:about 10:about 1:about 8:about 3, respectively. In an exemplary embodiment, a combination of the invention is listed in Table A.

TABLE A

| AMINO ACID | AMOUNT |
| --- | --- |
| Histidine | 0.20 g |
| Isoleucine | 1.35 g |
| Leucine | 5.08 g |
| Lysine | 2.12 g |
| Methionine | 0.42 g |
| Phenylalanine | 0.85 g |
| Threonine | 1.17 g |
| Valine | 1.39 g |
| Tryptophan | 0.42 g |

TABLE A-continued

| AMINO ACID | AMOUNT |
|---|---|
| Citrulline | 1.50 g |
| L-Carnitine | 0.50 g |

Amino acids may be supplied as peptides of intact protein or, preferably, in their free form. If not obtained commercially, individual amino acids may be produced by methods well known in the art, including chemical synthesis or use of recombinant microorganisms. A skilled artisan will appreciate that all amino acids except glycine may exist in more than one isomeric form—specifically, as a D-isomer or an L-isomer. Combinations of the present invention are preferably comprised of L amino acids.

In another aspect, combinations of the invention may further comprise one or more additional nutrients. The term "nutrient", as used herein, refers to prebiotics, vitamins, carbohydrates, fiber, fatty acids, sulfates, minerals, antioxidants, and other food ingredients used in subject's metabolism which are taken in from its environment. Suitable vitamins may include, but are not limited to: vitamin B1, vitamin B2, vitamin B3, vitamin B5, vitamin B6, vitamin B9, vitamin B12, lipoic acid, vitamin A, biotin, vitamin K, vitamin C, vitamin D, and vitamin E. Suitable minerals may include, but are not limited to compounds containing: iron, copper, magnesium, manganese, molybdenum, nickel, and zinc. Suitable enzyme cofactors may include, but are not limited to: adenosine triphosphate (ATP), S-adenosyl methionine (SAM), coenzyme B, coenzyme M, coenzyme Q, glutathione, heme, methanofuran, and nucleotide sugars. Suitable lipids may include, but are not limited to, fatty acids, glycerolipids, glycerophospholipids, sphingolipids, sterol lipids, prenol lipids, saccharolipids and polyketides. Non-limiting examples of fatty acids include myristoleic acid, palmitoleic acid, sapienic acid, oleic acid, elaidic acid, vaccenic acid, linoleic acid, linoelaidic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, hexadecatrienoic acid, alpha-linolenic acid, stearidonic acid, eicosatetraenoic acid, eicosapentaenoic acid, heneicosapentaenoic acid, docosapentaenoic acid, clupanodonic acid, docasehaenoic acid, tetracosapentaenoic acid, and tetracosahexaenoic acid. Additional non-limiting examples of nutrients may include Thiamin, Riboflavin, Niacin, Folate, Pantothenic acid, Calcium, Phosphorus, Magnesium, Manganese, Iron, Zinc, Copper, Selenium, Sodium, Potassium, betacarotene, retinol, alphatocopherol, betatocopherol, gammatocopherol, deltatocopherol, alphatoctrienol, betatoctrienol, gammatocotrienol, deltatocotrienol, apo-8-carotenal, trans-lycopene, cis-lycopene, trans-beta-carotene, and cis-beta-carotene, caffeine. In some embodiments, combinations of the invention further comprise one nutrient. In other embodiments, combinations of the invention further comprise at least one nutrient. For example, a combination of the invention may comprise 1, 2, 3, 4, 5, 6, 7, 8, 9, 10 or more nutrients. In still other embodiments, combinations of the invention further comprise two or more nutrients. In preferred embodiments, combinations of the invention further comprise at least one nutrient selected from the group consisting of omega-3 fatty acid and biotin. In other preferred embodiments, combinations of the invention further comprise two nutrients selected from the group consisting of omega-3 fatty acid and biotin. The overall contribution of the one or more nutrients to the total weight of the combination is substantially less than the contribution of the plurality of amino acids. Generally, the one or more nutrients comprise no more than about 10% by weight, preferably no more than about 5% by weight, more preferably no more than about 3% by weight of the combination. In preferred embodiments, the one or more nutrient is biotin. In other preferred embodiments, the one or more nutrient is one or more omega-3 fatty acid. In other preferred embodiments, the one or more nutrient is biotin and one or more omega-3 fatty acid. In an exemplary embodiment, a combination of the invention comprising one or more nutrient is listed in Table B or Table C.

TABLE B

| COMPONENT | AMOUNT |
|---|---|
| Histidine | 0.20 g |
| Isoleucine | 1.35 g |
| Leucine | 5.08 g |
| Lysine | 2.12 g |
| Methionine | 0.42 g |
| Phenylalanine | 0.85 g |
| Threonine | 1.17 g |
| Valine | 1.39 g |
| Tryptophan | 0.42 g |
| Citrulline | 1.50 g |
| L-carnitine | 0.50 g |
| Biotin | 150 μg |
| Omega-3 fatty acids | 450 mg |

TABLE C

| COMPONENT | AMOUNT |
|---|---|
| Histidine | 0.20 g |
| Isoleucine | 1.35 g |
| Leucine | 5.08 g |
| Lysine | 2.12 g |
| Methionine | 0.42 g |
| Phenylalanine | 0.85 g |
| Threonine | 1.17 g |
| Valine | 1.39 g |
| Tryptophan | 0.42 g |
| Biotin | 150 μg |
| Omega-3 fatty acids | 450 mg |

II. Formulations

In each of the above embodiments, amino acids and nutrients (when present) may be formulated for animal or human use. In some embodiments, each amino acid and nutrient (when present) is formulated separately. In other embodiments, two or more amino acids and nutrients (when present) are formulated together. In still other embodiments, all the amino acids and nutrients comprising a combination of the invention are formulated together. The one or more formulations may then be processed into one or more dosage forms that can be administered together, sequentially, or over a period of time (for example, over 1 minute, 10 minutes, 30 minutes, 1 hour, 3 hours, 6 hours, 9 hours, 12 hours, 18 hours, 24 hours, or more). Administration can be performed using standard effective techniques, including oral, parenteral (e.g. intravenous, intraperitoneal, subcutaneous, intramuscular), buccal, sublingual, or suppository administration. The term orally, as used herein, refers to any form of administration by mouth, including addition of a composition to animal feed or other food product. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Methods of preparing compositions for animal or human use are well known in the art. For instance, a composition may be generally formulated as a liquid composition, a solid composition or a semi-solid composition. Liquid compositions include, but are not limited to, aqueous suspensions, solutions, emulsions, elixirs, or syrups. Liquid composition will typically include a solvent carrier selected from a polar solvent, a non-polar solvent, or a combination of both. The choice of solvent will be influenced by the properties of the components of the composition. For example, if the components are water-soluble, a polar solvent may be used. Alternatively, if the components of the composition are lipid-soluble, a non-polar solvent may be used. Suitable polar and non-polar solvents are known in the art. Semi-solid compositions include douches, suppositories, creams, and topicals. Dry compositions include, but are not limited to, reconstitutable powders, chewable tablets, quick dissolve tablets, effervescent tablets, multi-layer tablets, bi-layer tablets, capsules, soft gelatin capsules, hard gelatin capsules, caplets, lozenges, chewable lozenges, beads, powders, granules, particles, microparticles, and dispersible granules. Formulations may include a combination of the invention along with an excipient. Non-limiting examples of excipients include binders, diluents (fillers), disintegrants, effervescent disintegration agents, preservatives (antioxidants), flavor-modifying agents, lubricants and glidants, dispersants, coloring agents, pH modifiers, chelating agents, antimicrobial agents, release-controlling polymers, and combinations of any of these agents.

Non-limiting examples of binders suitable for the formulations of various embodiments include starches, pregelatinized starches, gelatin, polyvinylpyrolidone, cellulose, methylcellulose, sodium carboxymethylcellulose, ethylcellulose, polyacrylamides, polyvinyloxoazolidone, polyvinyl-alcohols, C12-C18 fatty acid alcohols, polyethylene glycol, polyols, saccharides, oligosaccharides, polypeptides, oligopeptides, and combinations thereof. The polypeptide may be any arrangement of amino acids ranging from about 100 to about 300,000 Daltons. In one embodiment, the binder may be introduced into the mixture to be granulated in a solid form including but not limited to a crystal, a particle, a powder, or any other finely divided solid form known in the art. In another embodiment, the binder may be dissolved or suspended in a solvent and sprayed onto the mixture in a granulation device as a binder fluid during granulation.

Non-limiting examples of diluents (also referred to as "fillers" or "thinners") include carbohydrates, inorganic compounds, and biocompatible polymers, such as polyvinylpyrrolydone (PVP). Other non-limiting examples of diluents include dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, saccharides such as sucrose, dextrose, lactose, microcrystalline cellulose, fructose, xylitol, and sorbitol, polyhydric alcohols; starches; pre-manufactured direct compression diluents; and mixtures of any of the foregoing.

Disintegrents may be effervescent or non-effervescent. Non-limiting examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Suitable effervescent disintegrants include but are not limited to sodium bicarbonate in combination with citric acid, and sodium bicarbonate in combination with tartaric acid.

Non-limiting examples of preservatives include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof. In an exemplary embodiment, the preservatives is an antioxidant, such as a-tocopherol or ascorbate, and antimicrobials, such as parabens, chlorobutanol or phenol.

Suitable flavor-modifying agents include flavorants, taste-masking agents, sweeteners, and the like. Flavorants include, but are not limited to, synthetic flavor oils and flavoring aromatics and/or natural oils, extracts from plants, leaves, flowers, fruits, and combinations thereof. Other non-limiting examples of flavors include cinnamon oils, oil of wintergreen, peppermint oils, clover oil, hay oil, anise oil, eucalyptus, vanilla, citrus oils such as lemon oil, orange oil, grape and grapefruit oil, fruit essences including apple, peach, pear, strawberry, raspberry, cherry, plum, pineapple, and apricot.

Taste-masking agents include but are not limited to cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo, MP3295A, Benecel MP824, and Benecel MP843; methylcellulose polymers such as Methocel® and Metolose®; Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol co-polymers such as Kollicoat IRO; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials. In other embodiments, additional taste-masking agents contemplated are those described in U.S. Pat. Nos. 4,851,226, 5,075,114, and 5,876,759, each of which is hereby incorporated by reference in its entirety.

Non-limiting examples of sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia rebaudiana (Stevioside); chloro derivatives of sucrose such as sucralose; sugar alcohols such as sorbitol, mannitol, sylitol, hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

Lubricants may be utilized to lubricate ingredients that form a composition of the invention. As a glidant, the lubricant facilitates removal of solid dosage forms during the manufacturing process. Non-limiting examples of lubricants and glidants include magnesium stearate, calcium stearate, zinc stearate, hydrogenated vegetable oils, sterotex, polyoxyethylene monostearate, talc, polyethylene glycol, sodium benzoate, sodium lauryl sulfate, magnesium lauryl sulfate, and light mineral oil. The composition will generally comprise from about 0.01% to about 10% by weight of a lubricant. In some embodiments, the composition will comprise from about 0.1% to about 5% by weight of a lubricant. In a further embodiment, the composition will comprise from about 0.5% to about 2% by weight of a lubricant.

Dispersants may include but are not limited to starch, alginic acid, polyvinylpyrrolidones, guar gum, kaolin, bentonite, purified wood cellulose, sodium starch glycolate, isoamorphous silicate, and microcrystalline cellulose as high hydrophilic-lipophilic balance (HLB) emulsifier surfactants.

Depending upon the embodiment, it may be desirable to include a coloring agent. Suitable color additives include but are not limited to food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in various embodiments.

Non-limiting examples of pH modifiers include citric acid, acetic acid, tartaric acid, malic acid, fumaric acid, lactic acid, phosphoric acid, sorbic acid, benzoic acid, sodium carbonate and sodium bicarbonate.

A chelating agent may be included as an excipient to immobilize oxidative groups, including but not limited to metal ions, in order to inhibit the oxidative degradation of the morphinan by these oxidative groups. Non-limiting examples of chelating agents include lysine, methionine, glycine, gluconate, polysaccharides, glutamate, aspartate, and disodium ethylenediaminetetraacetate ($Na^2EDTA$).

An antimicrobial agent may be included as an excipient to minimize the degradation of the compound according to this disclosure by microbial agents, including but not limited to bacteria and fungi. Non-limiting examples of antimicrobials include parabens, chlorobutanol, phenol, calcium propionate, sodium nitrate, sodium nitrite, $Na^2EDTA$, and sulfites including but not limited to sulfur dioxide, sodium bisulfite, and potassium hydrogen sulfite.

Release-controlling polymers may be included in the various embodiments of the solid dosage compositions incorporating compounds according to this disclosure. In one embodiment, the release-controlling polymers may be used as a tablet coating. In other embodiments, including but not limited to bilayer tablets, a release-controlling polymer may be mixed with the granules and other excipients prior to the formation of a tablet by a known process including but not limited to compression in a tablet mold. Suitable release-controlling polymers include but are not limited to hydrophilic polymers and hydrophobic polymers.

Suitable hydrophilic release-controlling polymers include, but are not limited to, cellulose acetate, cellulose diacetate, cellulose triacetate, cellulose ethers, hydroxyethyl cellulose, hydroxypropyl cellulose, hydroxypropyl methylcellulose, microcrystalline cellulose, nitrocellulose, crosslinked starch, agar, casein, chitin, collagen, gelatin, maltose, mannitol, maltodextrin, pectin, pullulan, sorbitol, xylitol, polysaccharides, ammonia alginate, sodium alginate, calcium alginate, potassium alginate, propylene glycol alginate, alginate sodium carmellose, calcium carmellose, carrageenan, fucoidan, furcellaran, arabicgum, carrageensgum, ghaftigum, guargum, karayagum, locust beangum, okragum, tragacanthgum, scleroglucangum, xanthangum, hypnea, laminaran, acrylic polymers, acrylate polymers, carboxyvinyl polymers, copolymers of maleic anhydride and styrene, copolymers of maleic anhydride and ethylene, copolymers of maleic anhydride propylene or copolymers of maleic anhydride isobutylene), crosslinked polyvinyl alcohol and poly N-vinyl-2-pyrrolidone, diesters of polyglucan, polyacrylamides, polyacrylic acid, polyamides, polyethylene glycols, polyethylene oxides, poly(hydroxyalkyl methacrylate), polyvinyl acetate, polyvinyl alcohol, polyvinyl chloride, polystyrenes, polyvinylpyrrolidone, anionic and cationic hydrogels, and combinations thereof.

The invention can also include compositions that can be created as a powder that can be added to food items, as a baked good (e.g., as cookies and brownies), and as a concentrate. The concentrate can be added to water or another ingestible liquid to create a nutritional beverage. The nutritional supplement is typically contained within a one-serving or multiple serving container such as a package, box, carton, wrapper, bottle or can. Where the nutritional supplement is prepared in the form of a concentrate that can be added to and mixed with a beverage, a bottle or can be used for packaging the concentrate. The nutritional supplement can also include water.

III. Methods of Increasing Muscle Protein Synthesis

The present invention also provides methods for increasing muscle protein synthesis, increasing muscle strength, increasing muscle function, or a combination thereof. The method comprises administering to a subject a combination comprising a plurality of essential amino acids and optionally non-essential amino acids and/or nutrients. Suitable combinations and formulations for administration are described above in Section I and Section II, respectively. Suitable subjects may include a human, a livestock animal, a companion animal, a laboratory animal, or a zoological animal. In a preferred embodiment, a subject is human. The magnitude of response may depend, in part, on the dose given, the exact combination of amino acids, the physiological condition and/or age of the subject, and/or the timing of administration in relation to performance of exercise.

Muscle mass and function are progressively lost with aging, so that by age of 60 many otherwise healthy human subjects have reached a threshold where function begins to be affected. In an aspect, administering a combination of the invention to any healthy subject may increase muscle protein synthesis, increase muscle strength, increase muscle function, or a combination thereof, though the magnitude of the response may vary depending on age and/or the physiological condition of the subject.

The loss of body protein frequently accompanies illness, whether the illness is short term or long term. In another aspect, administering a combination of the invention to a subject that lost body protein as a result of illness may increase muscle protein synthesis, increase muscle strength, increase muscle function, or a combination thereof in the subject. In another aspect, administering a combination of the invention to a subject at risk of or experiencing muscle atrophy may increase muscle protein synthesis, increase muscle strength, increase muscle function, or a combination thereof. Non-limiting examples of subjects at risk of or experiencing muscle atrophy include humans with a sedentary lifestyle, people with seated jobs, medical conditions that limit movement, subjects that are bedridden, subjects who are away from Earth's gravity, subjects with an injury to a nerve that connects to muscle, and subjects at risk f or diagnosed with a disease affecting the nerves that control muscles. Non-limiting examples of diseases, disorders or conditions in which muscle atrophy occurs includes polio, Guillan-Barre syndrome, chronic obstructive pulmonary disease, congestive heart failure, acute coronary syndrome, chronic heart failure, cardiac cachexia, cancer, sarcopenia, spinal cord injury, osteoarthritis, arthritis, stroke, malnutrition, muscular dystrophy (e.g. Becker, congenital, Duchenne, Distal, Emery-Dreifuss, Facioscapulohumeral, Limb-Girdle, Oculopharyngeal), spinal muscular atrophy (e.g. ALS, motor neuron disease, infantile progressive spinal muscular atrophy, intermediate spinal muscular atrophy, juvenile spinal muscular atrophy, adult spinal muscular atrophy), inflammatory myopathies (e.g. dermatomyositis, polymyositis), diseases of the peripheral nerve (e.g. Carcot-Marie tooth disease, Dejerine-Sottas disease, Friedreich's ataxia), diseases of the neuromuscular junction (Myasthenia gravis, Lambert-Eaton syndrome), metabolic diseases of the muscle (acid maltase deficiency, carnitine deficiency, carnitine palmityl transferase deficiency, Debrancer enzyme deficiency, Lactate dehydrogenase deficiency, Mitochondrial deaminase deficiency, Phophorylase deficiency, Phosphofructokinase deficiency, Phosphoglycerate kinase deficiency), other myopathies (central core disease, hyperthyroid myopathy, myotonia congenita, myotubular myopathy, paramytonia congenita, periodic paralysis-hypokalemic-hyperkalemic), or any other disease or condition that requires a subject to be immobilized or on bed rest, especially chronic heart failure and cardiac cachexia.

Suitable subjects may be of any age, including at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 8, 88, 89, 90, 91, 92, 93, 94, 95, 96, 97, 98, 99, at least 100 or more years of age. A subject may also be less than one year of age.

In some embodiments, a method of the invention comprises administering to a subject a combination comprising phenylalanine, valine, threonine, tryptophan, methionine, leucine, isoleucine, lysine, and histidine in a w/w ratio of about 4:about 6:about 5:about 2:about 2:about 25:about 7:about 10:about 1, respectively. In other embodiments, a method of the invention comprises administering to a subject a combination comprising phenylalanine, valine, threonine, tryptophan, methionine, leucine, isoleucine, lysine, and histidine in a w/w ratio of about 4:about 6:about 5:about 2:about 2:about 25:about 7:about 10:about 1, respectively wherein the amino acids are at least about 80% of the total weight of the combination. In other embodiments, a method of the invention comprises administering to a subject a combination comprising phenylalanine, valine, threonine, tryptophan, methionine, leucine, isoleucine, lysine, histidine and citrulline in a w/w ratio of about 4:about 6:about 5:about 2:about 2:about 25:about 7:about 10:about 1:about 8, respectively. In other embodiments, a method of the invention comprises administering a combination comprising phenylalanine, valine, threonine, tryptophan, methionine, leucine, isoleucine, lysine, histidine and citrulline in a w/w ratio of about 4:about 6:about 5:about 2:about 2:about 25:about 7:about 10:about 1:about 8, respectively, wherein the ten amino acids are at least about 95% of the total weight of the combination. In other embodiments, a method of the invention comprises administering a combination comprising phenylalanine, valine, threonine, tryptophan, methionine, leucine, isoleucine, lysine, histidine, citrulline and L-carnitine in a w/w ratio of about 4:about 6:about 5:about 2:about 2:about 25:about 7:about 10:about 1:about 8:about 3, respectively. In an exemplary embodiment a method of the invention comprises administering a combination listed in Table A, Table B, or Table C. In preferred embodiments, a combination of the invention is administered to a subject with chronic heart failure or cardiac cachexia.

In an exemplary embodiment, a method of the invention comprises administering to a subject a combination comprising phenylalanine, valine, threonine, tryptophan, methionine, leucine, isoleucine, lysine, histidine, citrulline and L-carnitine in a w/w ratio of about 4:about 6:about 5:about 2:about 2:about 25:about 7:about 10:about 1:about 8:about 3, respectively, wherein the subject has chronic heart failure.

In an exemplary embodiment, a method of the invention comprises administering to a subject a combination comprising phenylalanine, valine, threonine, tryptophan, methionine, leucine, isoleucine, lysine, histidine, citrulline and L-carnitine in a w/w ratio of about 4:about 6:about 5:about 2:about 2:about 25:about 7:about 10:about 1:about 8:about 3, respectively, wherein the combination further comprises biotin, omega-3 fatty acids or a combination thereof, and wherein the subject has chronic heart failure.

In another exemplary embodiment, a method of the invention comprises administering to a subject a combination comprising phenylalanine, valine, threonine, tryptophan, methionine, leucine, isoleucine, lysine, histidine, citrulline and L-carnitine in a w/w ratio of about 4:about 6:about 5:about 2:about 2:about 25:about 7:about 10:about 1:about 8:about 3, respectively, wherein the combination further comprises biotin, omega-3 fatty acids or a combination thereof, and wherein the subject has chronic heart failure and is at least 50 years old, more preferably at least 60 years old, even more preferably at least 65 years old.

In another exemplary embodiment, a method of the invention comprises administering to a subject a combination listed in Table A, wherein the subject has chronic heart failure.

In another exemplary embodiment, a method of the invention comprises administering to a subject a combination listed in Table A, wherein the subject has chronic heart failure and is at least 50 years old, more preferably at least 60 years old, even more preferably at least 65 years old.

In another exemplary embodiment, a method of the invention comprises administering to a subject a combination listed in Table B, wherein the subject has chronic heart failure.

In another exemplary embodiment, a method of the invention comprises administering to a subject a combination listed in Table B, wherein the subject has chronic heart failure and is at least 50 years old, more preferably at least 60 years old, even more preferably at least 65 years old.

In another exemplary embodiment, a method of the invention comprises administering to a subject a combination comprising phenylalanine, valine, threonine, tryptophan, methionine, leucine, isoleucine, lysine, histidine, citrulline and L-carnitine in a w/w ratio of about 4:about 6:about 5:about 2:about 2:about 25:about 7:about 10:about 1:about 8:about 3, respectively, wherein the subject has cardiac cachexia.

In another exemplary embodiment, a method of the invention comprises administering to a subject a combination comprising phenylalanine, valine, threonine, tryptophan, methionine, leucine, isoleucine, lysine, histidine, citrulline and L-carnitine in a w/w ratio of about 4:about 6:about 5:about 2:about 2:about 25:about 7:about 10:about 1:about 8:about 3, respectively, wherein the combination further comprises biotin, omega-3 fatty acids or a combination thereof, and wherein the subject has cardiac cachexia.

In another exemplary embodiment, a method of the invention comprises administering to a subject a combination comprising phenylalanine, valine, threonine, tryptophan, methionine, leucine, isoleucine, lysine, histidine, citrulline and L-carnitine in a w/w ratio of about 4:about 6:about 5:about 2:about 2:about 25:about 7:about 10:about 1:about 8:about 3, respectively, wherein the combination further comprises biotin, omega-3 fatty acids or a combination thereof, and wherein the subject has cardiac cachexia and is at least 50 years old, more preferably at least 60 years old, even more preferably at least 65 years old.

In another exemplary embodiment, a method of the invention comprises administering to a subject a combination listed in Table A, wherein the subject has cardiac cachexia.

In another exemplary embodiment, a method of the invention comprises administering to a subject a combination listed in Table A, wherein the subject has cardiac cachexia and is at least 50 years old, more preferably at least 60 years old, even more preferably at least 65 years old.

In another exemplary embodiment, a method of the invention comprises administering to a subject a combination listed in Table B, wherein the subject has cardiac cachexia.

In another exemplary embodiment, a method of the invention comprises administering to a subject a combination listed in Table B, wherein the subject has cardiac cachexia and is at least 50 years old, more preferably at least 60 years old, even more preferably at least 65 years old.

The frequency of administration may be once, twice, three times or more daily, or once, twice, three times or more per week or per month, as needed as to produce the desired effect. The amount administered to the subject can and will vary depending upon the subject (e.g. age, weight, health status), and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

In some embodiments, a combination of the invention may be at least 5 grams in weight. For example, a combination may be at least 5, at least 6, at least 7, at least 8, at least 9, at least 10, at least 11, at least 12, at least 13, at least 14, at least 15, at least 16, at least 17, at least 18, at least 19, at least 20 grams or more in weight. In other embodiments, a combination of the invention may be about 5 to about 10 grams, about 10 to about 15 grams, about 15 to about 20 grams, about 5 to about 15 grams, about 10 to about 20 grams, or about 5 to about 20 grams in weight. In a preferred embodiment, a combination of the invention may be about 7 to about 15 grams in weight.

An increase in muscle protein synthesis may be measured by any method known in the art. For example, rates of protein synthesis and breakdown in muscle and blood have been measured for many years using radioactively labeled amino acids or amino acids labeled with stable isotopes. See for example, *Yale J Biol Med* 1997; 70(1): 65-76, incorporated herein by reference. Measurement of 3-methyhistidine excretion in urine or arteriovenous difference in 3-methylhistidine is used as a measure of the unidirectional rate of muscle protein breakdown. Total body skeletal mass can be measured using dual-energy X-ray (DEXA) absorptiometry or by CT; see, for example, *Am J Clin Nutr* 2002; 76:378-83, and *J Appl Physiol* 1985 incorporated herein by reference. Methods for measuring muscle strength or function are also well known in the art. For example, change in muscle strength and function can be assessed using basic standardized tests as described in *B J Nutr* 2012; 108: S88-93 or in Lu et al. (2012) "Strength and Functional Measurement for Patients with Muscular Dystrophy" Muscular Dystrophy, Dr. Madhuri Hegde (Ed.), each hereby incorporated by reference.

In some embodiments, a method of the invention may increase muscle protein synthesis by at least 2-fold. For example, muscle protein synthesis may increase at least 2-fold, at least 3-fold, at least 4-fold, at least 5-fold, at least 6-fold, at least 7-fold, at least 8-fold, at least 9-fold, at least 10-fold or more following administration of a combination of the invention. In some embodiments, a method of the invention may increase muscle strength by at least 2-fold. For example, muscle strength may increase at least 2-fold, at least 3-fold, at least 4-fold, at least 5-fold, at least 6-fold, at least 7-fold, at least 8-fold, at least 9-fold, at least 10-fold or more following administration of a combination of the invention. In some embodiments, a method of the invention may increase muscle function by at least 2-fold. For example, muscle function synthesis may increase at least 2-fold, at least 3-fold, at least 4-fold, at least 5-fold, at least 6-fold, at least 7-fold, at least 8-fold, at least 9-fold, at least 10-fold or more following administration of a combination of the invention. In other embodiments, a method of the invention may increase muscle protein synthesis, muscle strength and muscle function, or a combination thereof. Methods for measuring muscle protein synthesis, muscle strength and muscle function are known in the art and further detailed in the Examples.

EXAMPLES

The following examples illustrate various iterations of the invention. However, those of skill in the art should, in light of the present disclosure, appreciate that many changes can be made in the specific embodiments which are disclosed and still obtain a like or similar result without departing from the spirit and scope of the invention. All patents, applications, published applications and other publications are incorporated by reference in their entirety.

Example 1

Combinations of Essential Amino Acids Stimulate Muscle Protein Synthesis without Exercise Applicants have surprisingly found that functional improvements in disabled and/or elderly patients can be achieved with a dietary supplement comprised of a combination of essential amino acids (EAAs), even in the absence of an exercise program. Stimulation of muscle protein synthesis is the metabolic basis for improvements in functional and metabolic functions of muscle. The studies herein demonstrate that only EAAs are needed to stimulate muscle protein synthesis, thereby reducing the amount of amino acids that must be given to elicit an effective response.

As shown in FIG. 1, anabolic resistance to amino acids in elderly patients can be overcome by using a supplement that contains a high proportion of leucine (e.g. about 40% of total EAAs). In these experiments, net protein synthesis was measured in the leg muscle of elderly volunteers over the age of 65 years before and after ingestion of 6.7 g of a mixture of EAAs in the profile in whey protein or a mixture of the same amount of EAAs with 40% leucine.

Figure 2:
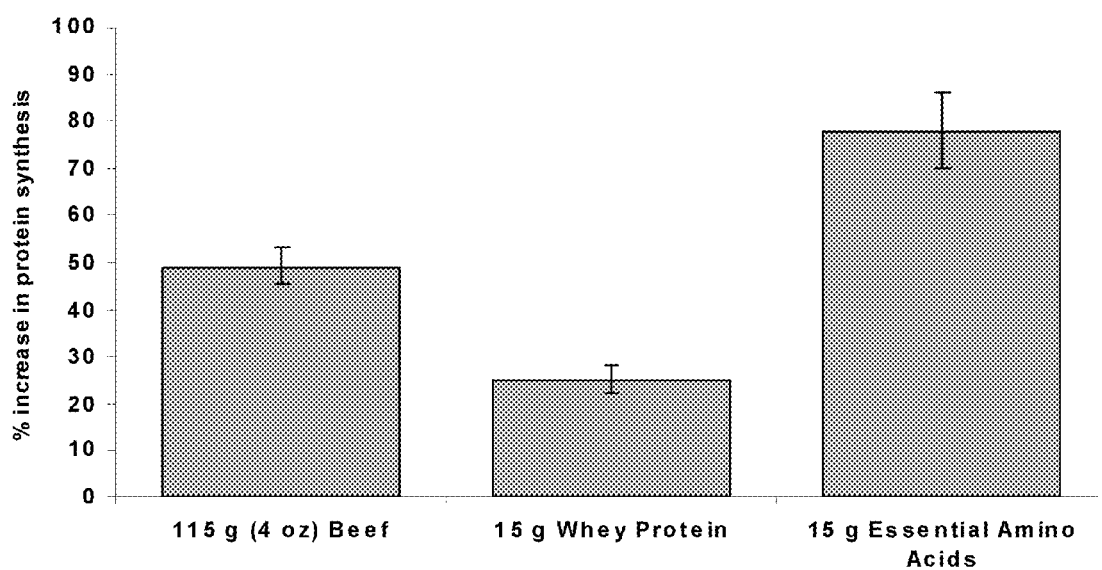
FIG. 2 depicts a graph showing the percent (%) increase in muscle protein synthesis in response to 15 grams of whey protein isolate, an EAA combination (Table C), or 115 g (4 oz.) of beef containing 39 grams protein. Protein synthesis was measured as described above.

After determining the transport rates of the individual EAAs into muscle, a combination of EAAs was formulated that delivered each amino acid intracellularly in proportion to the requirement for that amino acid as a component of muscle protein. The result is a formulation (Table C) that is much more effective in stimulating muscle protein synthesis than a high-quality protein such as whey or an intact food source of a high quality protein such as a beef patty (FIG. 2).

Figure 3:
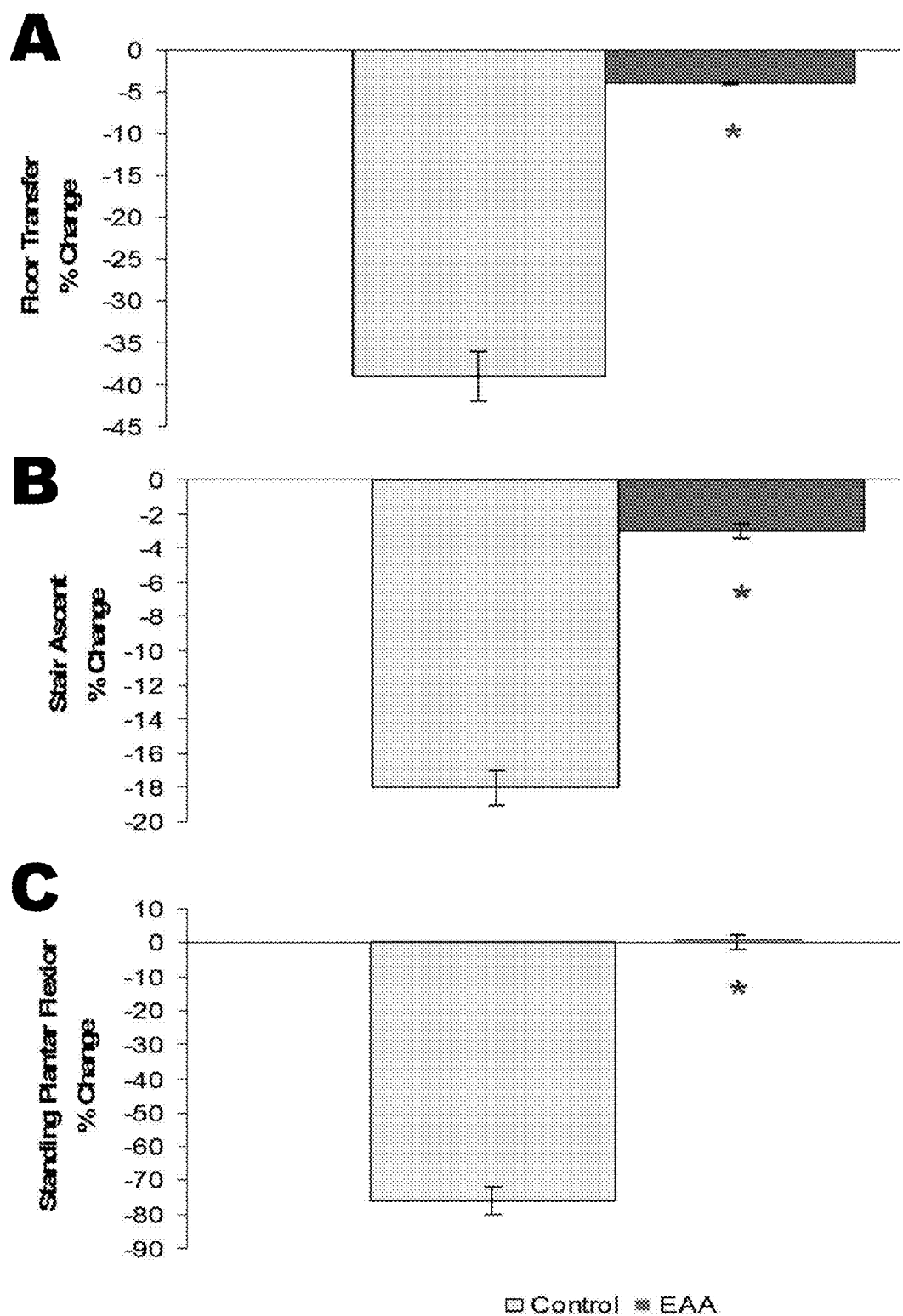
FIG. 3 depicts graphs showing that dietary supplementation with a combination of EAAs (Table C) ameliorated the detrimental effects of strict bed rest on parameters of physical function. Physical function was measured using basic standardized tests, including floor transfer (A), stair ascent (B), and standing plantar flexior (C).

FIG. 3 shows that the improvement in muscle protein synthesis observed after administration of the EAA formulation in Table C translates to improvements in practical outcome measures. For example, the losses in functional capacity that result from enforced bed rest in both young and old were almost completely ameliorated by a daily supplement of the EAA mixture. Further, EAA supplementation of free-living elderly volunteers for 16 weeks increased strength and functional capacity (Borsheim E, Q U Bui, S Tissier, H Kobayashi, A A Ferrando, R R Wolfe "Effect of amino acid supplementation on muscle mass, strength and physical function in elderly" (2008) Clin Nutr 27(2):189-195).

A high-leucine/protein mixture was also able to overcome anabolic resistance to conventional supplement intake in the highly-inflammatory states of cancer, and in patients recovering from hip-replacement surgery. Furthermore, the effectiveness of the EAA formulation is not reduced by insulin resistance.

Figure 4:
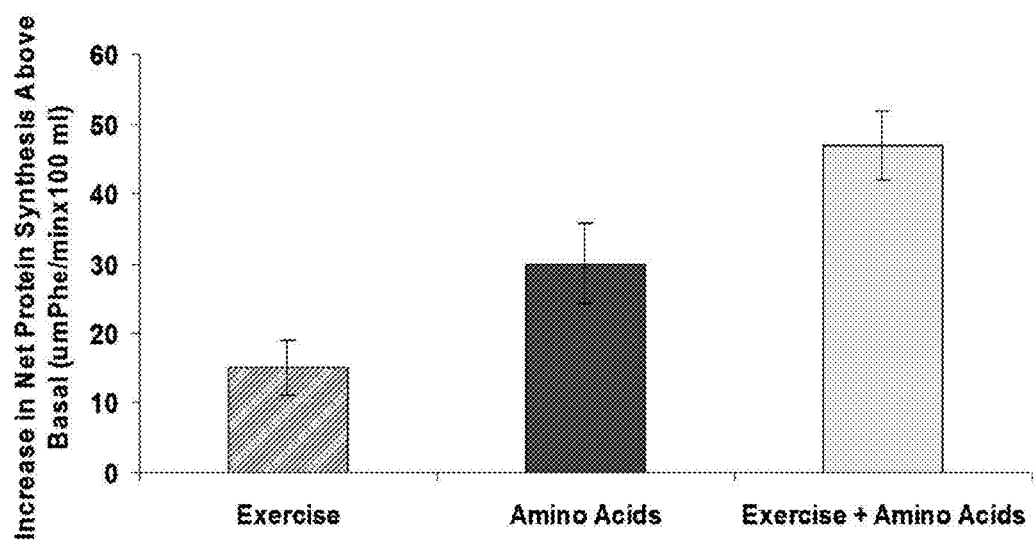
FIG. 4 depicts a graph showing the increase in net protein synthesis above base (y-axis) in the leg muscle of normal volunteers after a strenuous resistance exercise (left), after intake of amino acids (middle), or both (right). In these experiments, subjects were administered a commercially-available intravenous formulation of amino acids (Travasol).

One important aspect of the present invention is that it shows a significant interaction with exercise. Even in young, healthy individuals resistance exercise induces only a modest stimulation of muscle protein synthesis (FIG. 4). The magnitude of response to exercise is less than the response to amino acid intake alone (FIG. 4). However, prior exercise "primes" the muscle to the anabolic action of amino acids, such that there is an additive effect of exercise plus amino acids. Thus, whereas exercise protocols alone may have limited success in patients with heart failure because of anabolic resistance of muscle, the combination of some level of activity with nutrient therapy will result in a synergistic interaction that produces a significantly greater response than from the exercise alone or the essential amino acid mixture alone.

Example 2

Citrulline Supplementation Stimulates Nitric Oxide Production and Increased Plasma Arginine Levels Preferred formulations of the invention incorporate an optimized proportion of citrulline, the precursor of the amino acid arginine. Arginine is derived from both endogenous and dietary sources. Under normal conditions, the body produces sufficient arginine to satisfy metabolic requirements and hence is not be necessary in a mixture of EAAs to stimulate muscle protein synthesis. However, in certain clinical circumstances including in elderly with heart failure, endogenous production is inadequate to meet all demands. We have recently found that arginine synthesis is decreased in elderly with heart failure because of a reduced availability of citrulline.

A deficiency in arginine may result in a variety of metabolic consequences, including a reduced rate of muscle protein synthesis, impaired immune function, and decreased synthesis of nitric oxide (NO). In clinical circumstances in which de novo synthesis of arginine from citrulline may be inadequate, dietary supplementation can be an effective approach. Published studies have shown dietary supplementation with arginine reduces blood pressure and improves right ventricular function in patients with heart failure. These improvements translated to increased duration until exhaustion on a treadmill walk. However, there are limitations in the use of supplemental arginine. Because of high utilization of orally-ingested arginine by the gut and high first-pass clearance by the liver, dietary supplementation with arginine is only marginally effective in raising peripheral arginine availability. Consequently, a large dose of arginine is necessary, and this can cause significant gastric distress. Dietary supplementation with citrulline is more effective in increasing arginine availability. In contrast to arginine, splanchnic clearance of citrulline is low, and the renal conversion of citrulline to arginine is normally efficient. In contrast to arginine, citrulline is well-tolerated.

Figure 5:
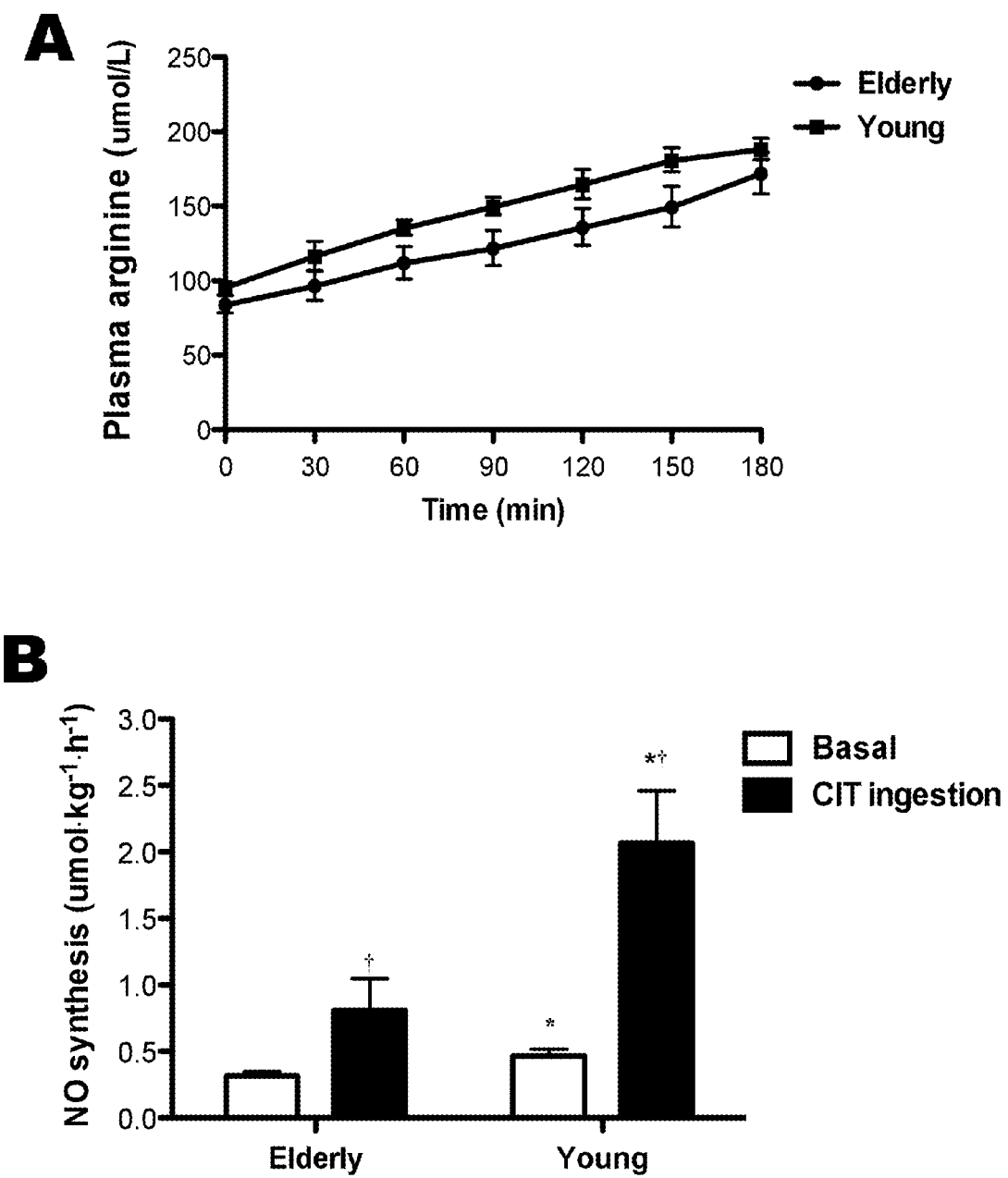
FIG. 5 depicts plasma arginine responses (A) and nitric oxide (NO) synthesis rates (B) in basal period and during ingestion of 3 g of citrulline (CIT) sip ingestion over 3 hours in elderly (n=8, 77±9y, 93±4 kg) and young individuals (n=8, 27±9y, 70±5 kg). NO synthesis rates are expressed per kg fat free mass. *Significantly different from the elderly, $p<0.05$; † Significantly different from basal period, $p<0.05$.

FIG. 5 shows the outcome of an isotopic tracer study in which multiple stable isotope tracers enabled quantification of the rates of arginine and citrulline synthesis as well as the rate of NO production. Briefly, elderly (n=8, 77±9y, 93±4 kg) and young individuals (n=8, 27±9y, 70±5 kg) ingested 3 grams of citrulline over 3 hours and plasma arginine response and nitric oxide (NO) synthesis rates were quantified. Notably, (1) NO synthesis was impaired in the elderly with heart failure as compared to young, healthy subjects, (2) ingestion of 3 g of citrulline effectively increased the concentration of arginine in the blood, and (3) citrulline ingestion stimulated production of NO. The extent of increase in NO production was less in elderly with heart failure than in young, but the increase in NO synthesis in elderly was physiologically significant. Thus, oral ingestion of citrulline is very effective in increasing peripheral arginine concentration and NO synthesis in elderly subjects with heart failure.

Figure 6:
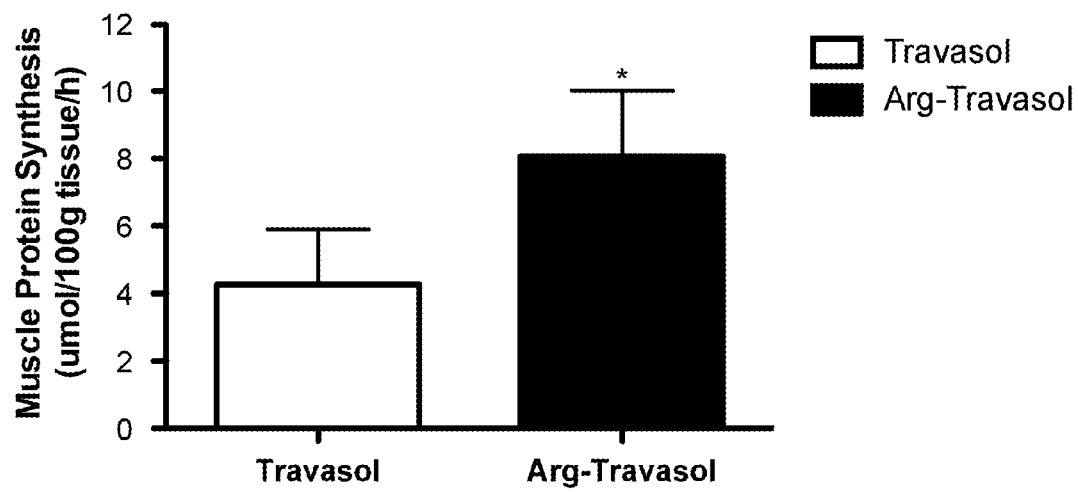
FIG. 6 depicts graphs showing leg muscle protein synthesis (umol phenylalanine/100 g tissue/h) in rabbits during an infusion of a balanced mixture of amino acids (Travasol, 1.5 ml/kg/h) or the same amino acid solution with extra arginine added Arg-Travasol (Travasol at 0.75 ml/kg/h; arginine at 205 umol/kg/h). *Significantly different from Arg-Travasol, $p<0.05$.

Arginine plays a role in the regulation of muscle protein synthesis beyond that of its contribution as a precursor of newly-synthesized protein. FIG. 6 shows the result of increasing the proportion of arginine in the mixture of an infusion of intravenous amino acids on muscle protein synthesis. The same amount of nitrogen was infused in both groups fundamentally in the form of a commercially-available intravenous formulation (Travasol), but in the arg-Travasol group extra arginine was added (and the rest of the amino acids reduced correspondingly).

The arginine effect on muscle protein synthesis is apparently independent of its effect on NO synthesis, as arginine administration was effective even when given when NO synthesis was pharmacologically blocked. See, for example, Zhang X-J, Chinkes D L, Wolfe R R "The anabolic effect of arginine on proteins in skin wound and muscle is independent of nitric oxide production" (2008) Clin Nutr 27:649-656.

Taken together, these data support adding citrulline to a formulation of EAAs in order to improve outcomes by increasing NO synthesis, as well as muscle protein synthetic response through increased arginine availability.

Example 3

Supplementation Improves Insulin Sensitivity

Figure 7:
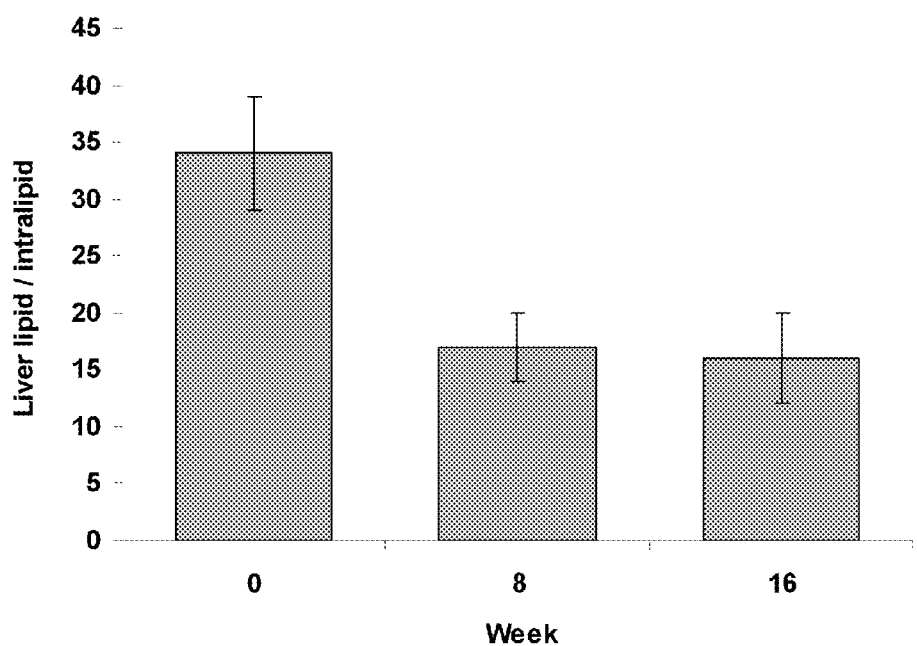
FIG. 7 depicts graphs showing liver fat in elderly human volunteers (n=16) at baseline and after 8 and 16 weeks of therapy with two doses of a combination of EAAs (11 g per dose; Table C) each day. Liver fat was measured using magnetic resonance spectroscopy (MRS). Units of liver fat are expressed in relation to a standard of Intralipid. The reduction in liver fat was associated with an improvement in insulin sensitivity.

Physical and cardiac function requires adequate ATP production to enable muscular contraction to occur. This not only involves functional vascular reactivity to enable increased oxygen and substrate delivery to contracting muscles, but also appropriate regulation of substrate metabolism and unimpaired oxidative capacity of mitochondria. Insulin resistance occurs commonly in elderly individuals with heart failure, particularly those who are obese, and the extent of insulin resistance is related to the deposition of fat in the liver. The EAA combination of Table C reduced hepatic fat (FIG. 7), which was related to an improvement in insulin sensitivity.

Example 4

Figure 8:
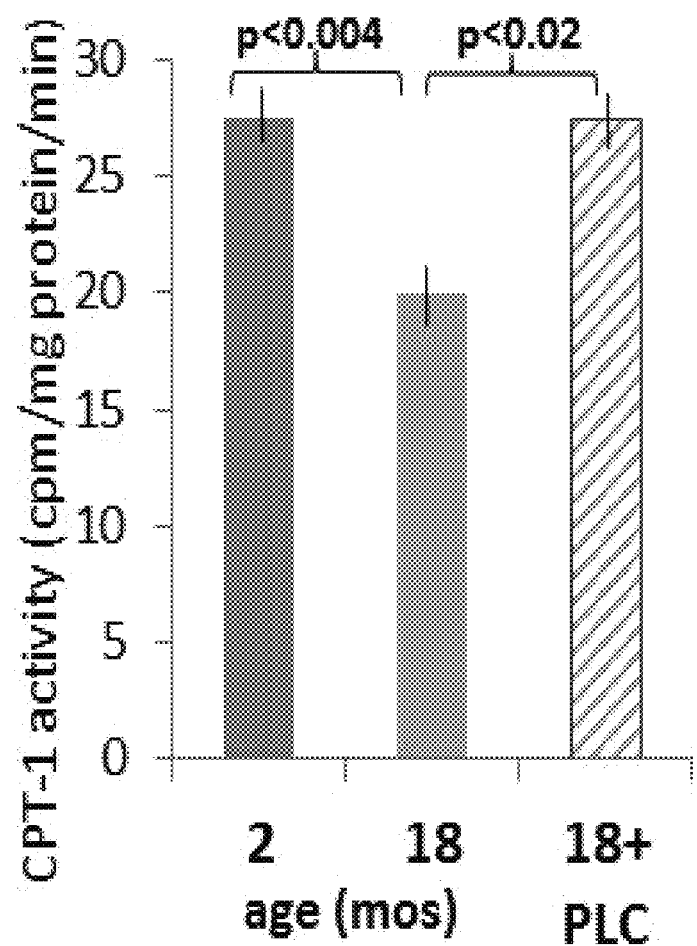
FIG. 8 depicts graphs showing carnitinepalmitoyltransferase (CPT)-1 activity decreases with age in mitochondria (2 vs 18 mos, p<0.004). Treatment with oral propionyl-L-carnitine (PLC) in old hearts restored CPT to that of young hearts (p<0.02) n=6.

Supplementation Increases the Number and Functional Capacity of Mitochondria in Subjects Appropriate regulation of energy substrate metabolism not only involves relatively normal insulin sensitivity, but also adequate number and functional capacity of mitochondria. One aspect of mitochondrial function is the rate of production of mitochondrial proteins. An EAA combination comprising phenylalanine, valine, threonine, tryptophan, methionine, leucine, isoleucine, lysine, and histidine stimulates mitochondrial proteins in skeletal muscle in human subjects (Bohe J, A Low, R R Wolfe, M J Rennie "Human muscle protein synthesis is modulated by extracellular but not intracellular amino acid availability: A dose response study" (2003) J Physiol 552:315-324); and leucine has recently been shown to stimulate mitochondrial biogenesis. In addition to adequate protein content in mitochondria, it is necessary that substrates, particularly long-chain fatty acids, are not limited in their ability to enter the mitochondria, or in their complete oxidation once inside the mitochondria. The capacity to oxidize fatty acids is reduced in patients with major inflammatory responses due to reduced carnitine palmitoyltransferase 1 (CPT1) activity. Unimpaired capacity to oxidize fatty acids is important because the energy to perform low-intensity exercise, including activities of daily living that individuals with heart failure often struggle with, is provided by the oxidation of fatty acids. As shown in FIG. 8, CPT-1 activity declines with advancing age and with oxidative stress in rodent hearts, and treatment of older hearts with propionyl-L-carnitine can restore CPT-1 activity to that of young hearts. Taken together, these data support adding L-carnitine to a formulation of EAAs in order to improve outcomes by increasing fatty acid oxidation.

What is claimed is:

1. A method for increasing muscle protein synthesis, increasing muscle strength, increasing muscle function, or a combination thereof, the method comprising administering to a subject with chronic heart failure, cardiac cachexia or a combination thereof a combination comprising phenylalanine, valine, threonine, tryptophan, methionine, leucine, isoleucine, lysine, histidine, citrulline and L-carnitine in a w/w ratio of about 4:about 6:about 5:about 2:about 2:about 25:about 7:about 10:about 1:about 8:about 3, respectively, and biotin, omega-3 fatty acids, or a combination thereof.

2. The method of claim 1, wherein the combination is the combination listed in Table B.

3. The method of claim 1, wherein the subject is a human.

4. The method of claim 1, wherein the subject is at risk of muscle atrophy.

5. The method of claim 1, wherein the subject is also diagnosed with a disease or condition selected from the group consisting of polio, Guillan-Barre syndrome, congestive heart failure, acute coronary syndrome, cancer, sarcopenia, spinal cord injury, osteoarthritis, arthritis, stroke, malnutrition, muscular dystrophy, spinal muscular atrophy, inflammatory myopathy, a disease of the peripheral nerve, a disease of the neuromuscular junction, and a metabolic disease of the muscle.

* * * * *